United States Patent [19]

Lill et al.

[11] Patent Number: 4,496,653
[45] Date of Patent: Jan. 29, 1985

[54] PROCESS FOR THE DETERMINATION OF ANTITHROMBIN-BM

[75] Inventors: Helmut Lill, Wielenbach; Jürgen Schrenk, Weilheim; Peter Wunderwald, Haunshofen, all of Fed. Rep. of Germany

[73] Assignee: Boehringer Mannheim GmbH, Mannheim-Waldhof, Fed. Rep. of Germany

[21] Appl. No.: 394,998

[22] PCT Filed: Oct. 8, 1981

[86] PCT No.: PCT/DE81/00170
    § 371 Date: Jun. 9, 1982
    § 102(e) Date: Jun. 9, 1982

[87] PCT Pub. No.: WO82/01377
    PCT Pub. Date: Apr. 29, 1982

[30] Foreign Application Priority Data
    Oct. 9, 1980 [DE] Fed. Rep. of Germany ....... 3038163
    Aug. 4, 1981 [DE] Fed. Rep. of Germany ....... 3050268

[51] Int. Cl.$^3$ ............... C12Q 1/56; C12Q 1/38
[52] U.S. Cl. .......................... 435/7; 435/13; 435/23
[58] Field of Search ............. 435/7, 13, 23, 24, 214, 435/810, 184

[56] References Cited

U.S. PATENT DOCUMENTS

| | | | |
|---|---|---|---|
| 4,070,245 | 1/1978 | Svendsen | 435/13 |
| 4,139,415 | 2/1979 | Yin et al. | 435/13 |
| 4,216,142 | 8/1980 | Ali | 435/13 |
| 4,234,682 | 11/1980 | Bartl et al. | 435/13 |
| 4,304,853 | 12/1981 | Jozefonvicz et al. | 435/13 |

FOREIGN PATENT DOCUMENTS

| | | |
|---|---|---|
| 0014184 | 8/1980 | European Pat. Off. . |
| 0048231 | 3/1982 | European Pat. Off. . |

OTHER PUBLICATIONS

"Heparin New Biochemical and Medical Aspects".
Kindness et al., Chemical Abstracts, 92: 208947w, 37 (1980).
Wunderwald et al., Chemical Abstracts, 96: 138774u, 387 (1982).
Kindness et al., Chemical Abstracts, 91: 83109v, 42 (1979).
Kindness et al., Chemical Abstracts, 91: 117860a, 97 (1979).
Kindness et al., Chemical Abstracts, 90: 165628, 355 (1979).

Primary Examiner—Esther M. Kepplinger
Attorney, Agent, or Firm—Felfe & Lynch

[57] ABSTRACT

For the determination of antithrombin-BM an antithrombin-BM-cofactor, thrombin and a determinable thrombin substrate are added to a sample solution and the splitting of the thrombin substrate is determined as a measure for the antithrombin-BM activity, whereby heparin, xylan, λ-carrageenan, dextran sulphate, mucopolysaccharide polysulphuric acid esters, pentosan polysulphates or short-chained heparin derivatives produced by the chemical or enzymatic splitting of heparin are used as cofactors.

10 Claims, 1 Drawing Figure

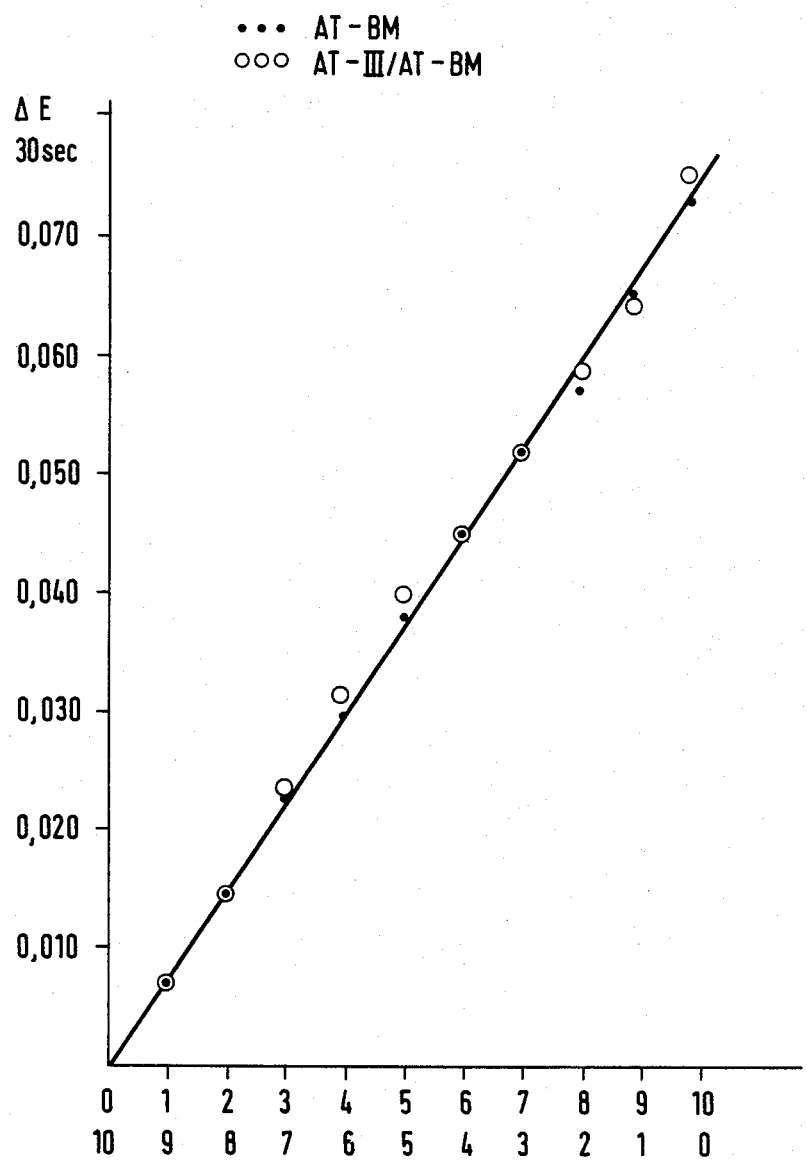

PROCESS FOR THE DETERMINATION OF ANTITHROMBIN-BM

The present invention is concerned with a process for the determination of a new thrombin inhibitor, which is called antithrombin BM, and with a reagent for carrying out the process.

The proteolytic enzyme thrombin plays an important part in the blood coagulation system. It is known that, in the coagulation system, a specific inactivator for thrombin is present which is able to inhibit thrombin in the presence of heparin and is called antithrombin III (AT III). Therefore, the use of heparin as an anticoagulent plays an important part in therapy and research. Furthermore, AT III, which is also called heparin cofactor, is an important component of test systems for the coagulation properties of plasma. However, AT III also inhibits thrombin in the absence of heparin in a time-dependent reaction and, apart from thrombin, also inhibits, for example, trypsin, plasmin and Factor Xa, and thus is relatively non-specific.

Surprisingly, we have now found a new specific thrombin inhibitor which differs from AT III in many respects. It is described in more detail in Federal Republic of Germany Patent Specification (Patent Application) No. 30 38 163.

The new thrombin inhibitor inhibits thrombin in the presence of dextran sulphate at least twice as strongly as in the presence of heparin, but plasmin and trypsin are practically not inhibited at all and thus it differs immunologically from AT III.

Since the new thrombin inhibitor binds to heparin less strongly than AT III, it is called AT-BM (antithrombin binding moderately to heparin).

Whereas, for optimum thrombin inhibition, AT III only requires a heparin concentration of the order of 0.02 USP/ml., in the case of AT-BM, the heparin concentration necessary for optimum thrombin inhibition is more than 1.0 USP/ml.

Whereas human AT III also inhibits, inter alia, Factor Xa, plasmin and trypsin and does not react substantially stronger with human thrombin as with bovine thrombin, the new human AT-BM is almost completely thrombin-specific and inhibits human thrombin much more strongly than bovine thrombin. Furthermore, the thrombin inhibition by AT III is much more strongly promoted by heparin than by other activators, such as dextran sulphate. On the other hand, in the case of AT-BM, a 2 to 3 times stronger thrombin inhibition is achieved with dextran sulphate than in the presence of heparin.

Whereas AT III inhibits thrombin in a time-dependent reaction, even in the complete absence of cofactors, such as heparin, under these conditions AT-BM shows no inhibiting action whatsoever.

On the basis of the above properties, the new thrombin inhibitor AT-BM according to the present invention can be used not only similarly to AT III in therapeutic and diagnostic processes and thus is an interesting research agent but can also be determined analytically in the presence of AT III.

Therefore, according to the present invention, the determination of AT-BM takes place by utilising the specificity differences towards AT III in the case of various cofactors.

Thus, according to the present invention, there is provided a process for the determination of antithrombin BM, wherein an antithrombin-BM cofactor, thrombin and a determinable thrombin substrate are added to a sample solution and the splitting of the thrombin substrate is determined as a measure of the antithrombin-BM activity, whereby (a) the specificity differences of antithrombin-BM towards antithrombin III in the presence of various amounts of the cofactors heparin, xylan or λ-carrageenan are utilised and the difference determined of the activities obtained in the case of high and low cofactor concentrations or (b) the antithrombin-BM activity is measured directly with dextran sulphate, mucopolysaccharide polysulphuric acid esters, pentosan polysulphates or short-chained heparin derivatives produced by the chemical or enzymatic splitting of heparin as cofactor.

The specificity differences of AT-BM in comparison with AT III in the presence of different amounts of heparin are given in the following Table 1:

TABLE 1

| | Specificity comparison of AT-BM/AT III | | | |
|---|---|---|---|---|
| | AT III (U/ml) | | AT-BM (U/ml) | |
| | 0.02 | 1.75 | 0.02 | 1.75 |
| | USP heparin/ml | | USP heparin/ml | |
| protease | test volume | | test volume | |
| bovine thrombin | | | | |
| total | 22.5 | 24.4 | 6.6 | 29.0 |
| "α-thrombin" | 25.9 | 25.6 | 3.7 | 40.3 |
| "β-thrombin" | 20.0 | 23.5 | 0.4 | 4.5 |
| human thrombin | | | | |
| total | 29.4 | 30.8 | 8.4 | 74.0 |
| "α-thrombin" | 23.0 | 31.7 | 6.2 | 101.1 |
| "β-thrombin" | 29.0 | 37.7 | 0.1 | 18.9 |
| Factor Xa | 5.6 | 29.5 | 0 | 0 |
| plasmin | 0 | 14.5 | 0 | 0.4 |
| trypsin | 23.5 | 16.5 | 0 | 0 |

Therefore, according to a preferred embodiment of the process according to the present invention, the total amount of AT-BM and AT III is determined at a concentration of 1 to 20 USP heparin per ml. and, in a parallel batch, AT III alone is determined at a low cofactor concentration of 0.01 to 0.03 USP heparin per ml. and the content of AT-BM determined from the difference between the two antithrombin amount determinations.

Instead of heparin, xylan or λ-carrageenan can be used as cofactor in analogous amounts.

In the case of the second embodiment of the process according to the present invention, as cofactors there are used dextran sulphate, mucopolysaccharide polysulphuric acid esters, pentosan polysulphates or a short-chained heparin derivative produced by the chemical or enzymatic splitting of heparin. Such heparin derivatives or heparin analogues are known and are commercially available, for example under the designations Arteparon (manufactured by the firm Luitpold, Munich, West Germany and described as mucopolysaccharide polysulphuric acid ester) or SP 54 (manufactured by the firm Bene-Chemie, Munich, West Germany and described as sodium pentosan polysulfate). In the case of concentrations of these cofactors of from about 2.5 to 25 μg./ml., only AT-BM is active so that, even in the presence of AT III, the content of AT-BM is selectively included.

Regardless of whether use is made of the difference method or of the direct specific AT-BM determination, for the determination use is preferably made of 0.01 to 0.1 U/ml. thrombin, 0.5 to 1000 μmol/ml. thrombin substrate and 10 to 250 mmol/liter of buffer (pH 7.5 to 8.5), in which case, up to 200 mmol/liter of sodium chloride and up to 50 IU/ml. of aprotonin can additionally also be added. However, the two last-mentioned substances are not essential and can also be omitted.

Furthermore, an addition of polyethylene glycol and/or of a complex former for heavy metals, for example ethylenediamine-tetraacetic acid and similar polyaminoacetates, has proved to be desirable.

The thrombin substrate can be any substrate known for thrombin determination, commercially available substrates which can be determined optically being preferred. These latter are low molecular peptides with a residue which can be split off and easily determined optically, Tos-Gly-Pro-Arg-pNa being especially preferred.

The buffer substance used can be any one which is effective in the range of from 7.5 to 8.5, tris buffer, triethanolamine buffer and tris-imidazole buffer being preferred.

In normal human plasma, AT-BM is present, as well as AT III and, on average, provides about 20% of the total antithrombin activity, the remaining approximately 80% being attributable to the AT III. Under certain circumstances, the ratio of AT-BM to AT III can change. This is shown by the experimental results given in the following Table 2:

TABLE 2

Antithrombin determination with bovine thrombin and 1.75 USP U/ml. heparin at 25° C.

| plasma | n | average total AT U/ml. | % total AT AT-BM | % total AT AT III |
|---|---|---|---|---|
| normal | 5 | 8.4 ± 0.3 | 20.8 ± 5.4 | 79.2 ± 5.4 |
| pregnant | 3 | 7.5 ± 2.5 | 14.0 ± 2.4 | 86.0 ± 2.4 |
| children | 6 | 6.1 ± 0.4 | 15.5 ± 0.5 | 84.5 ± 0.5 |
| marcumar | 8 | 5.7 ± 1.4 | 11.4 ± 4.5 | 88.5 ± 3.9 |
| suspected hepatitis | 3 | 4.6 ± 1.9 | 10.0 ± 5.6 | 90.0 ± 5.6 |
| serum | 3 | 3.9 ± 0.7 | 32.0 ± 4.4 | 68.0 ± 4.4 |

As already mentioned, the cofactor specificity of the new AT-BM is different from that of AT III. In particular, in the case of AT III, the highest inhibiting capacity is achieved in the presence of heparin, whereas in the case of AT-BM, substantially high inhibition values can be achieved with dextran sulphate. The values determined are given in the following Table 3:

TABLE 3

Comparison of the cofactor specificity of AT III/AT-BM in the case of the inhibition of bovine thrombin

| cofactor (25 μg./ml.) | antithrombin activity U/ml. of AT III | antithrombin activity U/ml. of AT-BM |
|---|---|---|
| heparin (15 μg./ml. = 1.75 USP/ml.) | 27.5 | 13.2 |
| λ-carrageenan | 5.4 | 9.3 |
| xylan | 6.3 | 1.2 |
| sodium dextran sulphate (M.W. = 500,00) | 4.1 | 33.0 |
| polystyrene sulphonate | 0 | 0 |

The properties of AT-BM also differ considerably from those of other known protease inhibitors in plasma. This can readily be seen from the following Table 4:

TABLE 4

Comparison of AT-BM with the known protease inhibitors in human plasma.

| inhibitor | M.W. in KD[1] | binding on heparin-seph. | immunol. cross-reaction with AT-BM | inhibition of thrombin | inhibition of Factor Xa | inhibition of plasmin | inhibition of trypsin | inhibition of chymotrypsin |
|---|---|---|---|---|---|---|---|---|
| α-1-antitrypsin | 54 | − | − | + | | + | + | + |
| α-1-antichymotrypsin | 68 | − | − | | | | | + |
| inter-α-trypsin inhibitor | 140 | + | − | + | | + | ± | ± |
| acid-stable proteinase inhibitor | 34 | CRM[2] | | | | | | |
| α2-macroglobulin | 725 | − | − | + | | + | + | + |
| α2-antiplasmin | 70 | − | | | | + | + | |
| antithrombin III | 67 | ++ | − | ++ | ++ | + | + | |
| C 1-esterase inactivator I | 105 | | | | | + | − | |
| C 1-esterase inactivator II | 96 | ± | CRM[2] − | | | + | − | |
| antithrombin-BM | 68–69 | + | not applicable | ++ | − | − | − | |

[1]KD = Kilodalton
[2]CRM = immunologically cross-reacting with one another

The present invention also provides a reagent for the determination of AT-BM, this reagent containing thrombin, a determinable thrombin substrate, buffer (pH 7.5 to 8.5), optionally sodium chloride and/or aprotonin, as well as one of the cofactors heparin, xylan, λ-carrageenan, dextran sulphate, mucopolysaccharide polysulphuric acid esters, pentosan polysulphates or a short-chained heparin derivatives produced by the chemical or enzymatic splitting of heparin.

A preferred reagent according to the present invention contains thrombin, heparin, aprotonin, polyethylene glycol, a complex former, sodium chloride, a thrombin substrate and a buffer.

Especially preferred embodiments of the reagent are characterised in that they contain thrombin, dextran sulphate, aprotonin, sodium chloride, buffer and a thrombin substrate; that the thrombin substrate consists of Tos-Gly-Pro-Arg-pNa; and that they contain 0.01 to 0.1 U/ml. of thrombin, 0.5 to 1000 μmol/ml. of thrombin substrate, 0 to 200 mmol/liter of sodium chloride, 0 to 50 IU/ml. of aprotinin and 10 to 250 mmol/liter of buffer.

The method for obtaining the thrombin inhibitor AT-BM is described in Federal Republic of Germany Patent Specification No. 30 38 163. It depends upon its different properties in comparison with AT III, for example towards heparin.

When serum, plasma or a fraction obtained therefrom is treated with insoluble, carrier-bound heparin and the latter, after removal of non-bound material, is eluted with an ion strength of 0.12 to 0.36 and at a pH in the range of from 6.5 to 8.3, then the AT-BM is obtained. AT III is not eluted under these conditions.

For the adjustment of the pH value range, use can be made of the buffer substances which buffer in the given range. The concentration of the buffer is preferably from about 0.005 to 0.1M. The best results are obtained at a pH value of from 7.5 to 8.0. Phosphate and tris buffers are preferred.

It is preferable to operate in the presence of a sequestering agent, such as ethylenediamine-tetraacetic acid (EDTA), the concentration of which is preferably from 5 to 20 mM.

The following Examples are given for the purpose of illustrating the present invention:

EXAMPLE 1

9 Parts of freshly collected blood are mixed with 1 part of 0.11 mol/liter sodium citrate and centrifuged at about 3000 r.p.m. 20 µl. of the citrate plasma thus obtained are diluted with 1.0 ml. of 0.9% sodium chloride solution.

5 ml. of a solution, which contains 0.1M tris HCl (pH 8.1), 0.15M sodium chloride, 0.01M EDTA, 1% polyethylene glycol, 6.5 IU aprotinin/ml. and 1.75 USP heparin/ml., are mixed with 0.25 ml. of a thrombin solution containing 0.5 U/ml. and left to stand for 30 minutes (AT reaction mixture). The determination is then carried out according to the following scheme at a measurement temperature of 25° C., using a cuvette of 1 cm. layer thickness and a wavelength of Hg 405 nm. The increase of the extinction is measured against air.

Pipette into synthetic resin cuvettes

| | starting value | sample |
| --- | --- | --- |
| 0.9% NaCl | 0.10 ml. | — |
| diluted plasma | — | 0.10 ml. |
| AT reaction mixture | 2.00 ml. | 2.00 ml. |
| mix and incubate for 5 minutes at 25° C. | | |
| 1.9 mM chromozyme TH[1] | 0.20 ml. | 0.20 ml. |
| mix, read off the initial extinction within 30 seconds and simultaneously start a stopwatch. Repeat the reading off after precisely 30, 60 and 90 seconds. | | |

[1] Tos—Gly—Pro—Arg—pNa.

Obtain the average value from the extinction differences per 30 seconds (ΔE/30 seconds) and use this for the calculation.

The total antithrombin activity is thus obtained. By repeating with a heparin concentration lowered to 0.02 USP/ml., the AT III concentration is obtained. From the difference of the total antithrombin activity minus AT III, there is obtained the amount of AT-BM.

EXAMPLE 2

| Reagents: | concentration of the solution ready for use |
| --- | --- |
| 1. buffer | |
| tris HCl | 100 mmol/liter, pH 8.1 |
| dextran sulphate (M.W. 500,000) | 1 mg./100 ml. |
| aprotinin | 6.5 IU/ml.* |
| sodium chloride | 150 mmol/liter |
| 2. thrombin | 0.5 U/ml. |
| 3. Chromozyme ® TH (Tos—Gly—Pro—Arg—pNA) | 1.9 mmol/liter |
| 4. mixture of 1 and 2 | |
| tris HCl | 90 mmol/liter, pH 8.1 |
| dextran sulphate | 0.9 mg/100 ml |
| aprotinin | 5.0 IU/ml. |
| sodium chloride | 136 mmol/liter |
| thrombin | 0.045 U/ml. |

*Inhibitor Units (trypsin, chromozyme TH, 25° C.)

Preparation of the Reagent Mixture (Mixture of 1 and 2)

Mix in a synthetic resin vessel and leave to stand for about 30 minutes at 25° C.: 10 ml. buffer (solution 1) and 1 ml. thrombin (solution 2).

Sample Preparation

For the determination, mix one part of citrate plasma with 200 parts of 0.9% sodium chloride solution (e.g. 50 µl. plasma and 10 ml. 0.9% sodium chloride solution).

| Determination batch | |
| --- | --- |
| Wavelength: | Hg 405 nm |
| Cuvette: | synthetic resin cuvette, 1 cm. layer thickness |
| Measurement temperature: | 25° C. |
| Measurement against air (extinction increase) | |

At least one thrombin blank (TB) is necessary for each series of measurements.

Pipette into synthetic resin cuvettes:

| | TB | sample |
| --- | --- | --- |
| 0.9% NaCl solution | 0.05 ml. | — |
| diluted plasma | — | 0.05 ml. |
| reagent mixture (4) | 1.0 ml. | 1.0 ml. |
| mix and incubate for 5 minutes at 25° C. | | |
| Solution 3 | 0.1 ml. | 0.1 ml. |
| mix and calculate ΔE/30 sec. | | |

Calculation:

$$\Delta E_{TB}/30 \text{ sec.} - \Delta E_{sample}/30 \text{ sec.} = \Delta E_{AT\text{-}BM}/30 \text{ sec.}$$

$$IU_{AT\text{-}BM}/\text{ml.} = \Delta E_{AT\text{-}BM}/30 \text{ sec.} \times 951.1$$

For the determinations, solutions were prepared of AT-BM and AT III with the following contents:
AT III: 12.5 IU/ml. 25° C.
AT-BM: 12.1 IU/ml. 25° C.

This concentration corresponds to the normal amount of AT III in human plasma.

In order to demonstrate the specificity of the determination even in the presence of AT III, the determination was carried out not only with the AT-BM solutions but also with a mixture of the two solutions. The procedure was thereby as follows:

1. Measurement of AT-BM

The AT-BM solution was diluted 1+100 with physiological saline (0.05 ml. sample+5.0 ml. sodium chloride solution).

For the determination of the measurement range, from this sample dilution there were prepared further dilutions with physiological saline (9 parts AT-BM+1 part NaCl; 8+2; 7+2 etc.) up to an end dilution of 1:1000.

Constant volumes (0.05 ml.) of the prepared AT-BM dilutions were then used in the test.

The result is shown in FIG. 1 of the accompanying drawing (• • • •). Within the selected limits, the test measures the inhibition values ($\Delta E_{AT-BM}$) proportionally.

2. Measurement of AT-BM in the presence of AT III 0.05 ml. of AT-BM solution was diluted with 0.05 ml. AT III solution and 4.95 ml. of physiological saline (corresponding to a 1+100 dilution of both components).

Successive dilutions were prepared from this sample solution as described above under 1.

Constant volumes (0.05 ml.) of the prepared dilutions were then used in the test.

The result is shown in FIG. 1 of the accompanying drawing (○ ○ ○ ○). Within the limits of exactitude of the test, the same results were obtained as with AT-BM alone. The test result is not influenced by AT III, only the AT-BM being measured.

Analogous results were obtained when the dextran sulphate was replaced by mucopolysaccharide polysulphuric acid esters, pentosan polysulphates or by the heparin derivatives described hereinbefore.

We claim:

1. A process for the determination of antithrombin-BM in a sample comprising
    adding, to the sample, an antithrombin-BM cofactor, thrombin and a determinable thrombin substrate;
    measuring the splitting of the thrombin substrate in the presence of a high concentration of cofactors, and in the presence of a low concentration of cofactors, the cofactors being selected from the group consisting of heparin, xylan and λ-carrageenan; and
    determining the antithrombin-BM activity from the difference between the measurement at high and at low cofactor concentration.

2. The process according to claim 1, wherein 1 to 20 USP heparin per ml. is used as the high concentration and 0.01 to 0.03 heparin per ml. is used as the low concentration.

3. The process according to claim 2 wherein polyethylene glycol and a complex former for heavy metals is added to the solution.

4. The process according to claim 3, wherein a solution is used which contains 0.012 U/ml. of thrombin, 6.5 IU of aprotinin per ml and 1% polyethylene glycol and which solution is 0.01 molar ethylenediamine-tetraacetic acid, 0.15 molar sodium chloride, 0.1 molar buffer and 0.19 mmolar determinable thrombin substrate.

5. The process according to claim 1, wherein use is made of 0.01 to 0.1 U/ml. of thrombin, 0.5 to 1000 μmol/ml. thrombin substrate, 0 to 200 mmol/liter sodium chloride, 0 to 50 IU/ml. of aprotonin and 10 to 250 mmol/liter of buffer (pH 7.5 to 8.5).

6. The process according to claim 1, wherein the thrombin substrate used is Tos-Gly-Pro-Arg-pNA.

7. A process for the determination of antithrombin-BM in a sample, comprising
    adding, to the sample, an antithrombin-BM cofactor, thrombin, and a determinable thrombin substrate, said cofactor being selected from the group consisting of dextran sulphate, mucopolysaccharide polysulphuric acid esters, pentosan polysulphates and short-chained heparin derivatives produced by the chemical or enzymatic splitting of heparin; and
    measuring the splitting of the thrombin substrate as a measure of the antithrombin-BM activity.

8. The process according to claim 7, wherein 2.5 to 25 μg. dextran sulphate or heparin fission product per ml. are used.

9. A process according to claim 7, wherein use is made of 0.01 to 0.1 U/ml. of thrombin, 0.5 to 1000 μmol/ml. thrombin substrate, 0 to 200 mmol/liter sodium chloride, 0 to 50 IU/ml. of aprotonin and 10 to 250 mmol/liter of buffer (pH 7.5 to 8.5).

10. A process according to claim 7, wherein a solution is used which contains 0.012 U/ml of thrombin, 6.5 IU of aprotinin per ml and 1% polyethylene glycol and which solution is 0.01 molar ethylenediamine-tetraacetic acid, 0.15 molar sodium chloride, 0.1 molar buffer and 0.19 mmolar determinable thrombin substrate.

* * * * *